United States Patent
Hamby et al.

(10) Patent No.: US 7,022,711 B2
(45) Date of Patent: Apr. 4, 2006

(54) 2-(4-PYRIDYL)AMINO-6-DIALKOXYPHENYL-PYRIDO[2,3-D]PYRIMIDIN-7-ONES

(75) Inventors: James Marino Hamby, Ann Arbor, MI (US); Sylvester Klutchko, Ann Arbor, MI (US); James Bernard Kramer, Sylvania, OH (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/343,847

(22) PCT Filed: Jul. 20, 2001

(86) PCT No.: PCT/US01/22881

§ 371 (c)(1),
(2), (4) Date: Feb. 4, 2003

(87) PCT Pub. No.: WO02/12238

PCT Pub. Date: Feb. 14, 2002

(65) Prior Publication Data

US 2003/0220345 A1    Nov. 27, 2003

Related U.S. Application Data

(60) Provisional application No. 60/223,083, filed on Aug. 4, 2000.

(51) Int. Cl.
| | |
|---|---|
| C07D 471/04 | (2006.01) |
| A61K 31/519 | (2006.01) |
| A61P 35/00 | (2006.01) |
| A61P 9/10 | (2006.01) |
| A61P 3/10 | (2006.01) |

(52) U.S. Cl. .................. 514/264.11; 544/279
(58) Field of Classification Search .............. None
See application file for complete search history.

(56) References Cited

U.S. PATENT DOCUMENTS

| 5,733,914 A | 3/1998 | Blankley et al. |
| 5,945,422 A | 8/1999 | Doherty et al. |
| 2003/0176700 A1* | 9/2003 | Tjiong et al. ............... 544/279 |
| 2003/0216415 A1* | 11/2003 | Beylin et al. ........... 514/264.11 |

OTHER PUBLICATIONS

PCT International Search Report PCT/US01/22881.

S. R. Klutchko, et al., "2-Substituted Aminopyrido[2,3-d] pyrimidin-7(8H)-ones. Structure-Activity Relationships Against Selected Tyrosine Kinases and in Vitro and in Vivo Anticancer Activity", J. Med. Chem., 1998, vol. 41, pp 3276-3292.

D. H. Boschelli, et al., "Synthesis and Tyrosine Kinase Inhibitory Activity of a Series of 2-Amino-8H-pyrido[2,3-d]pyrimidines: Identification of Potent, Selective Platelet-Derived Growth Factor Receptor Tyrosine Kinase Inhibitors", J. Med. Chem., 1998, vol. 41, pp 4365-4377.

S. Trumpp-Kallmeyer, et al., "Development of a Binding Model to Protein Tyrosine Kinases for Substituted Pyrido [2,3-d]pyrimidine Inhibitors", J. Med. Chem., 1998, vol. 41, pp 1752-1763.

R. L. Panek, et al., In Vitro Pharmacological Characterization of PD 166285, a New Nanomolar Potent and Broadly Active Protein Tyrosine Kinase Inhibitor:, J. Pharmacol. Exp. Ther., 1997, vol. 283 No. 3, pp 1433-1444.

* cited by examiner

*Primary Examiner*—Mark L. Berch
(74) *Attorney, Agent, or Firm*—Wendy L. Hsu; Steven R. Eck

(57) ABSTRACT

This invention provides antiangiogenic compounds of the Formula (I), which are useful for treating diseases, resulting from uncontrolled cellular proliferation such as cancer, atherosclerosis, rheumatoid arthritis, and psoriasis.

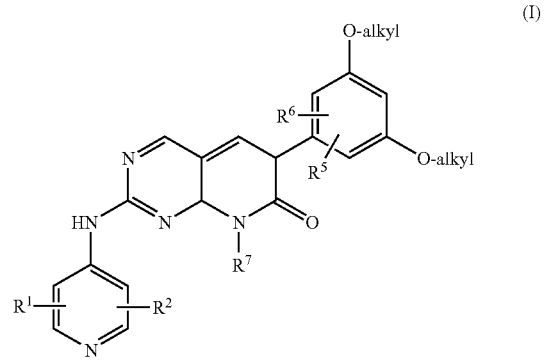

20 Claims, No Drawings

2-(4-PYRIDYL)AMINO-6-DIALKOXYPHENYL-PYRIDO[2,3-D]PYRIMIDIN-7-ONES

RELATED APPLICATIONS

This application is a continuation of copending application having U.S. Ser. No. 10/343,847, filed on Feb. 4, 2003, which claims priority of PCT/US01/22881 filed on Jul. 20, 2001, which claims benefit of U.S. Provisional Application U.S. Ser. No. 60/223,083, filed on Aug. 4, 2000.

FIELD OF THE INVENTION

This invention provides antiangiogenic 2-(4-pyridyl)amino-6-dialkoxyphenyl-pyrido[2,3-d]pyrimidine-7-ones that are useful for treating cancer, atherosclerosis, rheumatoid arthritis, restenosis, psoriasis, diabetic retinopathy, macular degeneration, and other diseases associated with aberrant blood vessel proliferation.

BACKGROUND OF THE INVENTION

Angiogenesis is the formation of capillaries from preexisting vessels, generally occurring in the embryo and adult mammalian organisms as part of normal growth and repair, such as wound healing. However, uncontrolled angiogenesis is also associated with cellular proliferative disorders such as cancer, diabetic retinopathy, macular degeneration, psoriasis, rheumatoid arthritis, atheroma, Kaposi's sarcoma, and haemangioma. Solid tumor growth and invasion depend upon an adequate blood supply to provide cellular growth factors, nutrients, and to remove metabolic by-products from active cell division.

Tumor angiogenesis involves a number of sequential and complex processes beginning with the production and release of angiogenic factors by tumor cells or their surrounding matrix, culminating in development of the tumor vasculature. This multistep cascade includes endothelial cell (EC) activation, proliferation, and migration, followed by tube formation and maturation. Angiogenic growth factors, such as basic fibroblast growth factor (FGF) and vascular endothelial growth factor (VEGF), which are expressed during growth of the tumor, are key modulators of EC function and the entire neovascular process. Accordingly, small molecular weight compounds that are specific and selective inhibitors of FGF and VEGF receptor tyrosine kinases on ECs are useful as antiangiogenic therapies for treating cancer and other diseases caused by uncontrolled cellular proliferation.

U.S. Pat. No. 5,733,914, incorporated herein by reference, describes a broad class of pyrido[2,3-d]pyrimidines that are said to be useful to treat cancer and other cellular proliferative diseases due to their ability to inhibit a wide variety of growth factor receptor tyrosine kinases such as platelet derived growth factor PDGF), epidermal growth factor (EGF), as well as VEGF and FGF. The compounds are substituted at the 6-position by aryl and heteroaryl groups, which groups may be substituted with various moieties including halo, alkyl, alkoxy, thio, thioalkyl, hydroxy, amino, and alkanoyl. The disclosure points to dihalophenyl as a preferred substituent on the pyrido[2,3-d]pyrimidine nucleus, and specifically the 2,6-dichlorophenyl as being the most preferred. The patent additionally describes a variety of possible substituent groups at the 2-position of the pyrido[2,3-d]pyrimidine nucleus, including arylamino, with phenylamino said to be the most preferred. These compounds suffer from lack of bioavailability, metabolic stability, and enzyme selectivity.

We have now discovered a series of pyrido[2,3-d]pyrimidines that are surprisingly more potent and selective as inhibitors of VEGF and FGF than the compounds described in U.S. Pat. No. 5,733,914, and which are bioavailable and stable in mammals. The present compounds are characterized as 2-[(4-pyridyl)amino]-6-(3,5-dialkoxyphenyl)-8H-pyrido[2,3-d]pyrimidin-7-ones. An object of this invention is to provide potent, selective, and metabolically stable inhibitors of VEGF and FGF, and a method of treating diseases resulting from uncontrolled cellular proliferation using such compounds.

SUMMARY OF THE INVENTION

This invention provides compounds characterized as 2-[(4-pyridyl)amino]-6-(3,5-dialkoxyphenyl)-8H-pyrido[2,3-d]pyrimidin-7-ones that are potent, selective, and metabolically stable inhibitors of the growth factor receptor tyrosine kinases known as VEGF and FGF. The invention more particularly provides compounds of Formula I

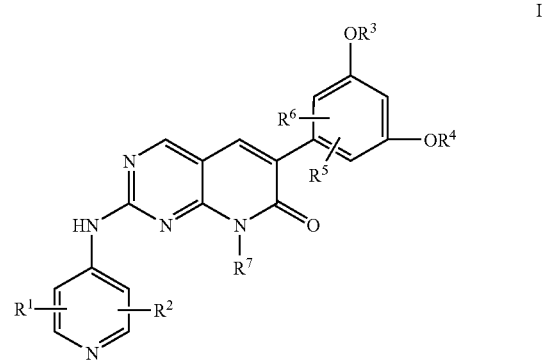

wherein:

$R^1$, $R^2$, $R^5$, and $R^6$ independently are hydrogen, halogen, $C_1$–$C_6$ alkyl, $C_1$–$C_6$ alkoxy, thio, thioalkyl, hydroxy, $C_1$–$C_6$ alkanoyl, —CN, —NO$_2$, $C_1$–$C_6$ alkanoyloxy, COOR$^8$, —CF$_3$, NR$^8$R$^9$, or $(X)_m$—$(CH_2)_n$—NR$^8$R$^9$, where $R^8$ and $R^9$ independently are hydrogen, $C_1$–$C_6$ alkyl, $C_1$–$C_6$ alkanoyl, or $R^8$ and $R^9$ taken together with the nitrogen to which they are attached complete a 5- to 7-membered ring;

X is NH or O;

m is 0 or 1;

n is 0 to 6; provided m and n are not both 0, $R^3$ and $R^4$ independently are $C_1$–$C_6$ alkyl and halo substituted $C_1$–$C_6$ alkyl;

$R^7$ is hydrogen, $C_1$–$C_6$ alkyl, $C_2$–$C_6$ alkenyl, $C_2$–$C_6$ alkynyl, or $C_3$–$C_6$ cycloalkyl;

and the pharmaceutically acceptable salts and solvates thereof.

Alternatively, $R^1$, $R^2$, $R^5$, and $R^6$ are independently hydrogen, halogen, $C_1$–$C_6$ alkyl, $C_1$–$C_6$ alkoxy, thio, thioalkyl, hydroxy, $C_1$–$C_6$ alkanoyl, —CN, —NO$_2$, $C_1$–$C_6$ alkanoyloxy, COOR$^8$, —CF$_3$, NR$^8$R$^9$, or $(X)_m$—$(CH_2)_n$—NR$^8$R$^9$, where $R^8$ and $R^9$ independently are hydrogen, $C_1$–$C_6$ alkyl, $C_1$–$C_6$ alkanoyl, or $R^8$ and $R^9$ taken together with the nitrogen to which they are attached can complete a ring having 3 to 7 carbon atoms and optionally containing 1, 2, or 3 heteroatoms selected from the group consisting of nitrogen, substituted nitrogen, oxygen, and sulfur.

Preferred compounds have Formula I wherein $R^1$, $R^2$, $R^5$, and $R^6$ are hydrogen, and $R^7$ is $C_1$–$C_6$ alkyl.

Another preferred group of compounds have Formula I wherein $R^3$ and $R^4$ both are methyl.

The most preferred compound of Formula I is 6-(3,5-dimethoxyphenyl)-8-ethyl-2-(pyridin-4-ylamino)-8H-pyrido[2,3-d]pyrimidin-7-one.

The invention also provides a method for treating diseases caused by uncontrolled cellular proliferation in a mammal comprising administering to the mammal an effective amount of a compound of Formula I. Typical diseases are cancers such as leukemia and breast cancer.

Accordingly, the present invention provides a method of treating uncontrolled angiogenesis in a mammal comprising administering to the mammal in need of treatment an antiangiogenic effective amount of a compound of Formula 1.

The present invention also provides a method of treating cancer in a mammal having cancer and in need of treatment comprising administering an effective amount of a compound of Formula I.

Furthermore, the present invention provides use of a compound of Formula I, or a pharmaceutically acceptable salt thereof for the manufacture of a medicament for treating any of the diseases or disease states mentioned above.

Additionally, the present invention provides use of a compound of Formula I, or a pharmaceutically acceptable salt thereof for treating any of the diseases or disease states mentioned above.

A further embodiment of this invention is a pharmaceutical composition comprising a compound of Formula I admixed with a pharmaceutically acceptable carrier, diluent, or excipient therefor.

DETAILED DESCRIPTION OF THE INVENTION

The compounds of the present invention can exist in unsolvated form as well as solvated forms, including hydrated forms. In general, the solvated forms, including hydrated forms, are equivalent to unsolvated forms and are intended to be encompassed within the scope of the present invention.

In the compounds of Formula I, the term "$C_1$–$C_6$ alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like. The term "$C_1$–$C_6$ alkyl" includes within its definition the term "$C_1$–$C_3$ alkyl".

The terms "halogen" and "halo" include fluoro, chloro, bromo, and iodo.

"Halo substituted $C_1$–$C_6$ alkyl" groups are the foregoing alkyl groups having one or more halo substituents. Examples include trifluoromethyl, perfluoropentyl, 1,2,3,-trichloropropyl, 2-chloro-4-fluorohexyl, and the like.

The terms "alkenyl" and "$C_2$–$C_6$ alkenyl" mean straight or branched hydrocarbon radicals having from 2 to 6 carbon atoms and 1 double-bond and includes ethenyl, 3-buten-1-yl, 2-ethenylbutyl, 3-hexen-1-yl, and the like.

The terms "alkynyl" and "$C_2$–$C_6$ alkynyl" mean a straight or branched hydrocarbon radical having from 2 to 6 carbon atoms and at least one triple bond. Typical $C_2$–$C_6$ alkynyl groups include propynyl, 2-butyn-1-yl, 3-pentyn-1-yl and the like.

"$C_3$–$C_6$ cycloalkyl" means a cyclic hydrocarbyl group such as cyclopropyl, cyclobutyl, cyclohexyl, and cyclopentyl.

"$C_1$–$C_6$ alkoxy" refers to the alkyl groups mentioned above binded through oxygen, examples of which include methoxy, ethoxy, isopropoxy, tert-butoxy, and the like.

"$C_1$–$C_6$ alkanoyl" refers to an alkyl group, as defined above, linked through a carbonyl, i.e.,

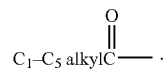

Such groups include formyl, acetyl, propionyl, butyryl, and isobutyryl.

"$C_1$–$C_6$ alkanoyloxy" refers to the alkanoyl groups mentioned above binded through oxygen.

The alkyl, alkenyl, alkoxy, and alkynyl groups described above may be substituted. The substituent groups which may be part of the alkyl, alkenyl, alkoxy, and alkynyl groups are $NR^8R^9$, phenyl, substituted phenyl, thio($C_1$–$C_6$)alkyl, $C_1$–$C_6$ alkoxy, hydroxy, carboxy, $C_1$–$C_6$ alkoxycarbonyl, halo, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1$–$C_6$ alkyl or $(CH_2)_n$Ph.

Examples of "$R^8$ and $R^9$ taken together with the nitrogen to which they are attached can complete a ring having 3 to 7 carbon atoms and optionally containing 1, 2, or 3 heteroatoms selected from the group consisting of nitrogen, substituted nitrogen, oxygen, and sulfur" includes, but is not limited to, pyrrolidine, piperidine, and piperazine. The 5- to 7-membered ring may be optionally substituted by $C_1$–$C_6$ alkyl.

Examples of substituted alkyl groups thus include 2-aminoethyl, 2-diethylaminoethyl, 2-dimethylaminopropyl, ethoxycarbonylmethyl, 2-piperidinoethyl, 3-phenylbutyl, methylsulfanylmethyl, methoxymethyl, 3-hydroxypentyl, 2-carboxybutyl, 4-chlorobutyl, 3-cyclopropylpropyl, 3-morpholinopropyl, piperazinylmethyl, and 2-(4-methylpiperazinyl) ethyl.

Examples of substituted alkenyl groups thus include 2-diethylaminoethenyl, 3-amino-2-butenyl, 3-(1-piperazinyl)-1-propenyl, 3-hydroxy-1-propenyl, 2-(1-s-triazinyl)ethenyl, 3-phenyl-3-pentenyl, and the like.

Examples of substituted alkynyl groups include 2-methoxyethynyl, 2-ethylsulfanylethynyl, 4-(1-piperazinyl)-3-(butynyl), 3-phenyl-5-hexynyl, 3-diethylamino-3-butynyl, 4-chloro-3-butynyl, 4-cyclobutyl-4-hexynyl, and the like.

Typical substituted alkoxy groups include aminomethoxy, trifluoromethoxy, 2-diethylaminoethoxy, 2-ethoxycarbonylethoxy, 3-pyrrolidinopropoxy, 3-hydroxypropoxy, 6-carboxyhexyloxy, and the like.

Further, examples of substituted alkyl, alkenyl, and alkynyl groups include dimethylaminomethyl, carboxymethyl, 4-diethylamino-3-buten-1-yl, 5-ethylmethylamino-3-pentyn-1-yl, 4-morpholinobutyl, 4-tetrahydropyridinylbutyl-3-imidazolidin-1-ylpropyl, 4-tetrahydrothiazol-3-yl-butyl, phenylmethyl, 3-chlorophenylmethyl, and the like.

The compounds of Formula I are capable of further forming pharmaceutically acceptable salts, including both pharmaceutically acceptable acid addition and/or base salts. All of these forms are within the scope of the present invention.

Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate and the like and gluconate, galacturonate (see, for example, Berge S. M., et al., "Pharmaceutical Salts," *J. of Pharmaceutical Science*, 1977;66:1–19).

The acid addition salts of the basic compounds are prepared by contacting the free base form with a sufficient amount of the desired acid to produce the salt in the conventional manner. The free base form may be regenerated by contacting the salt form with the base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge S. M., supra., 1977).

The base addition salts of acidic compounds (for example when $R^3$ is a carboxy alkyl group such as carboxymethyl or 3-carboxybutyl) are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

While the forms of the invention herein constitute presently preferred embodiments, many others are possible. It is not intended herein to mention all of the possible equivalent forms or ramifications of the invention. It is understood that the terms used herein are merely descriptive rather than limiting, and that various changes may be made without departing from the spirit or scope of the invention.

Compounds of Formula I may be prepared according to the syntheses outlined in Schemes 1–7. Although these schemes often indicate exact structures, the methods apply widely to analogous compounds of Formula I, given appropriate consideration to protection and deprotection of reactive functional groups by methods standard to the art of organic chemistry. For example, hydroxy groups, in order to prevent unwanted side reactions, generally need to be converted to ethers or esters during chemical reactions at other sites in the molecule. The hydroxy protecting group is readily removed to provide the free hydroxy group. Amino groups and carboxylic acid groups are similarly derivatized to protect them against unwanted side reactions. Typical protecting groups, and methods for attaching and cleaving them, are described fully by Greene and Wuts in *Protective Groups in Organic Synthesis*, John Wiley and Sons, New York, (2$^{nd}$ Ed; 1991), and McOmie, *Protective Groups in Organic Chemistry*, Plenum Press, New York, 1973.

Scheme 1 describes a typical method for preparing pyrido [2,3-d]pyrimidines of Formula I. The synthesis starts by reacting the appropriate 4-(substituted amino)-2-methylsulfanyl-pyrimidine-5-carboxaldehyde (*J. Med. Chem.*, 1998, 41(22):4365–4377 or *J. Med. Chem.*, 1998;41(17):3276–3292) with an acetonitrile reagent in the presence of a base and suitable solvent to afford the condensed 6-(aryl)-8-(substituted)-2-methylsulfanyl-8H-pyrido [2,3-d]pyrimidin-7-ylideneamine product. The reaction is typically carried out in an unreactive solvent such as dioxane, 2-ethoxyethanol, dimethylformamide, tetrahydrofuran, and the like. Typical bases that can be utilized in the reaction include sodium methoxide, potassium hexamethyldisilane, 1,8-diazabicyclo[5.4.0]undec-7-ene, sodium hydride, potassium tert-butoxide, lithium diethylamide, and the like. Typical arylacetonitriles which can be employed include 3,5-dimethoxyphenylacetonitrile, 2,6-dimethyl-3,5-dimethoxyphenylacetonitrile, 2-methyl-3,5-dimethoxyphenylacetonitrile, 2,6-dichloro-3,5-dimethoxyphenylacetonitrile, 2-chloro-3,5-dimethoxyphenylacetonitrile, 2-fluoro-3,5-dimethoxyphenylacetonitrile, 2,6-difluoro-3,5-dimethoxyphenyl, 3,5-trifluoromethoxyphenylacetonitrile, and the like. The reaction is typically carried out at elevated temperatures of about 50° C. to about 200° C., and is generally substantially complete within about 2 to 24 hours. The product, a 6-(aryl)-8-(substituted)-2-methylsulfanyl-8H-pyrido[2,3-d]pyrimidin-7-ylideneamine is readily isolated by adding water to the reaction mixture, which generally causes precipitation of the product. The imine product can be further purified if needed by recrystallization from solvents such as ethyl acetate, acetone, isopropanol and the like, or by chromatography over solid supports such as silica gel.

The 6-(aryl)-8-(substituted)-2-methylsulfanyl-8H-pyrido [2,3-d]pyrimidin-7-ylideneamines are useful therapeutic agents, as well as intermediates and are readily converted to the corresponding 7-keto derivative by acylation with a suitable acylating reagent such as acetic anhydride followed by acid catalyzed hydrolysis of the resulting acylimino group. Hydrolysis of the acylimino group is generally substantially complete after heating with an aqueous mineral acid such as hydrochloric acid, sulfuric acid, phosphoric acid, or the like for a about 5 to about 24 hours at about 60° C. to about 200° C. The product, a 6-(aryl)-8-(substituted)-2-methylsulfanyl-8H-pyrido[2,3-d]pyrimidin-7-one, is readily isolated by removal of the reaction solvent by evaporation under reduced pressure, and crystallization from common solvents such as ethyl acetate, ethanol, dimethylformamide, and the like.

The methylthio group of the 6-(aryl)-8-(substituted)-2-methylsulfanyl-8H-pyrido[2,3-d]pyrimidin-7-one is readily oxidized to the respective sulfoxide or sulfone by oxidizing reagents such as m-chloroperbenzoic acid, hydrogen peroxide, peracetic acid, 3-phenyl-2-(phenylsulfonyl)oxaziridine or the like. In Scheme 1, the 2-methylthio group of the pyrimidone intermediate is oxidized to the corresponding sulfoxide using 3-phenyl-2-(phenylsulfonyl)oxaziridine in a suitable solvent such as dichloromethane at room temperature.

The displacement of the sulfoxide group of the penultimate intermediate with 4-aminopyridine or a substituted 4-aminopyridine derivative provides compounds of Formula I. In method A of Scheme 1, the displacement is accomplished by reacting the anion of the 4-aminopyridine reagent with the sulfoxide intermediate. The anion is generated at −78° C. to −40° C. in suitable solvent such as tetrahydrofuran, dioxane, or the like using a strong base such as butyllithium or the like. The sulfoxide is added as a solid or in a solvent such as dimethylformamide to the anion and reacted for 1 to 24 hours at a temperature of −78° C. to 30° C. Alternatively as described for method B of Scheme 1, the sulfoxide intermediate and the 4-aminopyridine reagent are directly fused together at temperatures of 80° C. to 200° C. Additionally, the reaction can be carried out as a concentrated mixture of the sulfoxide intermediate and excess 4-aminopyridine reagent in a solvent such as DMSO at temperatures of 80° C. to 180° C. The product can be purified by crystallization from solvents such as ethyl acetate, dimethylformamide, isopropanol and the like, or by chromatography over solid supports such as silica gel.

Scheme 2 shows an alternative route to Scheme 1 for the condensation of the 4-(substituted amino)-2-methylsulfanyl-pyrimidine-5-carboxaldehyde with an acetonitrile reagent. In Scheme 2 the aldehyde is condensed directly with a substituted phenyl acetic acid ester in the presence of a suitable base such as 1,8-diazabicyclo[5.4.0]undec-7-ene. The reaction can be accomplished neat or in a solvent such as dimethylformamide or dimethyl sulfoxide to afford the condensed 6-(aryl)-8-(substituted amino)-2-methylsulfanyl-8H-pyrido[2,3-d]pyrimidin-7-one product. The pyrimidinone can then be elaborated to compounds of Formula I as described in Scheme 1.

Scheme 3 describes another method for preparing compounds of Formula I starting from the commercially available ethyl 2-methylthio-4-chloro-pyridin-5-carboxylate. The 4-chloro group of the starting pyrimidine is displaced by a primary amine (NHR$^7$) in a suitable solvent such as dimethylformamide to afford the corresponding ethyl 2-methylthio4-(substituted amino)-pyridin-5-carboxylate. Excess of the reacting amine can be employed to scavenge the HCl byproduct produced in the reaction. The temperature for the displacement depends upon the nature of the amine being reacted. Generally, aliphatic amines react at room temperature while less nucleophilic amines such as aromatic amines require higher temperatures. The subsequent oxidation of the methylthio group with an oxidant such as 3-phenyl-2-(phenylsulfonyl)oxaziridine in a solvent such as dichloromethane at ambient temperature provides the corresponding sulfoxide intermediate. As described in Scheme 1, the sulfoxide is displaced by 4-aminopyridine or related substituted 4-aminopyridine derivative by direct displacement with the amine at higher temperatures. Alternatively, the sulfoxide can be reacted with the anion of the 4-aminopyridine reactant that is generated from the reaction of the amine with a strong base such as butyllithium to give the 2-(4pyridylamino)-4-(substituted)-pyridin-5-carboxylate. The subsequent reduction of the ester group with a common reducing agent such as LAH, provides the corresponding alcohol. Oxidation of the alcohol with MnO$_2$ or other suitable oxidant affords the penultimate aldehyde. Cyclization to compounds of Formula I is accomplished as described in Scheme 2 by reaction with an appropriately substituted phenyl acetic acid ester under basic conditions.

Starting from the 6-(aryl)-8-substituted-2-methanesulfinyl-8H-pyrido[2,3-d]pyrimidin-7-one intermediate described in Schemes 1 and 2, compounds of Formula I can be prepared according to Scheme 4. The reaction of the sulfoxide with ammonia gas dissolved in a suitable solvent such as methanol, dioxane, and the like or with aqueous ammonia hydroxide at temperatures of 0° C. to 100° C. affords the 6-(aryl)-8-substituted-2-amino-8H-pyrido[2,3-d]pyrimidin-7-one intermediate. Deprotonation of the 2-amino group with a strong base such as butyllithium, sodium hydride, or the like gives rise to the corresponding anion in situ which is further reacted with a 4-halo pyridine derivative to give compounds of Formula I. The halogen leaving group represented by X in Scheme 4 of the 4-halo pyridine derivative can be chlorine, bromine, iodine, or fluorine.

Scheme 5 describes another variation of the chemical synthesis of compounds of Formula I. The 4-chloro group of the commercially available ethyl 2-methylthio-4-chloro-pyridin-5-carboxylate starting pyrimidine is displaced using ammonia gas in a suitable solvent such as methanol or with aqueous ammonium hydroxide to give ethyl 2-methylthio-4-amino-pyridin-5-carboxylate. Excess of the reacting amine can be employed to scavenge the HCl byproduct produced in the reaction. Reduction of the ester using LAH or other suitable reducing agent such as diborane, NaBH$_4$—NiCl$_2$ or the like affords the corresponding alcohol. Oxidation with MnO$_2$ or other suitable oxidant produces the aldehyde intermediate 4-amino-2-methylsulfanyl-pyrimidine-5-carboxaldehyde. The condensation of the aldehyde with the appropriately substituted phenyl acetate derivative yields the cyclized product. Alkylation of the 8-position with X-R7 is accomplished by first forming the anion of the cyclized intermediate with a base such as NaH, Cs$_2$CO$_3$, DBU, and the like. Subsequent treatment of the anion with the alkylating reagent X-R7 where X represents a leaving group such as Cl, Br, I, CH$_3$SO$_3$, or the like gives the desired 6-(aryl)-8-substituted-2-methylsulfanyl-8H-pyrido[2,3-d]pyrimidin-7-one intermediate. Elaboration to compounds of Formula I is accomplished oxidizing the methylthio group to the sulfoxide and the nucleophilic displacement of the sulfoxide with an 4-amino pyridine derivative as described previously in Scheme 1.

Scheme 6 shows a preferred process for preparing the invention compounds of Formula I that comprises reacting a 4-aminopyridine with a 2-(4-imino-4H-pyridin-1-yl)-6-aryl-8-substituted-8H-pyrido[2,3-d]pyrimidine-7-one. The reaction is typically carried out by mixing the 4-aminopyridine and the imino-4H-pyridin-1-yl reactant in an unreactive organic solvent such as dimethylsulfoxide or acetonitrile in the presence of a base such as potassium carbonate and at an elevated temperature of about 80° C. to 100° C. The reaction proceeds through a dimer intermediate, namely a 2-{4-[(6-aryl-7-oxo-8-substituted-8H-pyrido[2,3-d]pyrimidine-2-yl)-imine]4H-pyridin-1-yl }-6-aryl-8-substituted-8H-pyrido[2,3-d]pyrimidine-7-one. This intermediate can be isolated if desired or used in situ, and further reaction with additional 4-aminopyridine affords the desired invention compound of Formula I. The 2-(4-imine-4H-pyridin-1-yl) starting material is prepared by reacting a 2-alkylsulfinyl pyridopyrimidine with a 4-aminopyridine acid addition salt at approximately room temperature.

The most preferred process for preparing the invention compounds comprises reacting a 4-aminopyridine with a 2-alkylsulfanyl pyridopyrimidine in the presence of a hydride such as lithium hydride or sodium hydride, or an alkali metal amide such as lithium amide. This reaction is illustrated in Scheme 7. The 4-aminopyridine and alkali metal base are generally mixed together in an unreactive organic solvent such as tetrahydrofuran and heated at about 50° C. for 1 to 2 hours. The alkylsulfanyl pyridopyrimidine is then added, and the mixture generally is heated at reflux for about 24 hours. The product is readily isolated in high yield and excellent purity.

As noted above, the compounds of the invention are basic in nature, by virtue of the pyridyl group and other nitrogen atoms in the rings, as well as substituent groups which is basic, such as amino groups for example. Such basic compounds readily form pharmaceutically acceptable salts with any number of inorganic and organic acids. The salts typically are crystalline, and generally are water soluble and are thus well-suited to oral administration and the like. Typical salts are formed with inorganic acids such as hydrochloric and sulfonic acid, as well as with organic acids such as acetic acid and methanesulfonic acid.

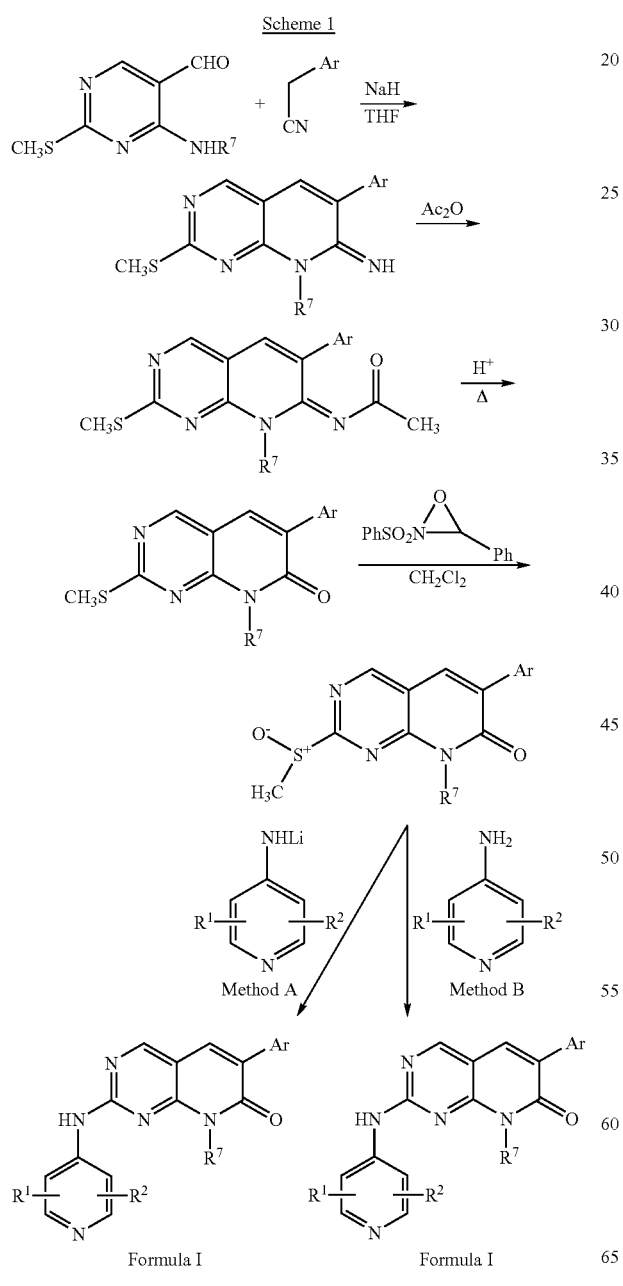

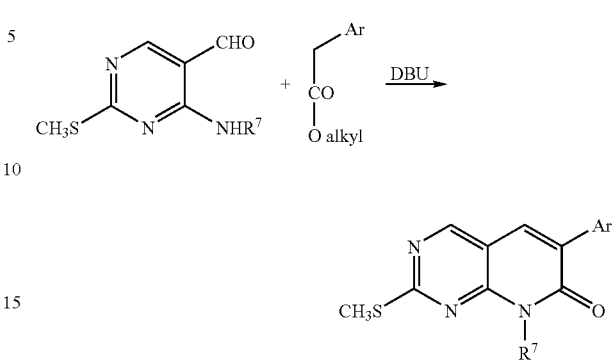

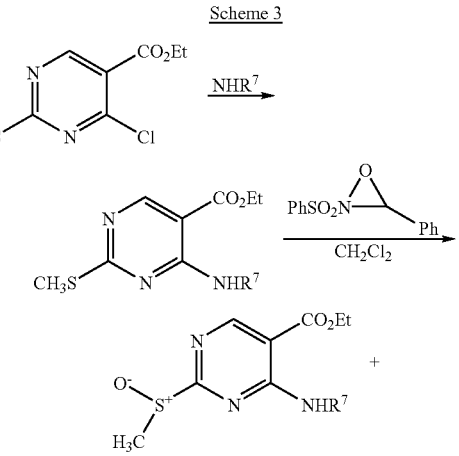

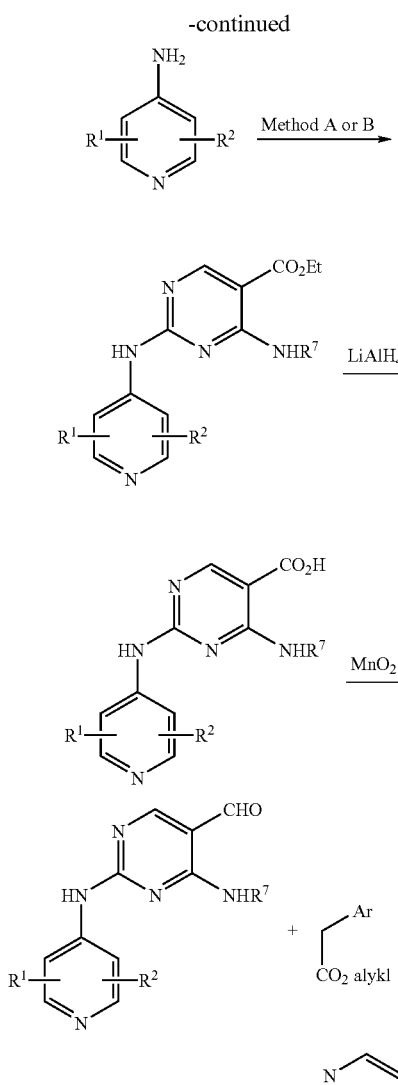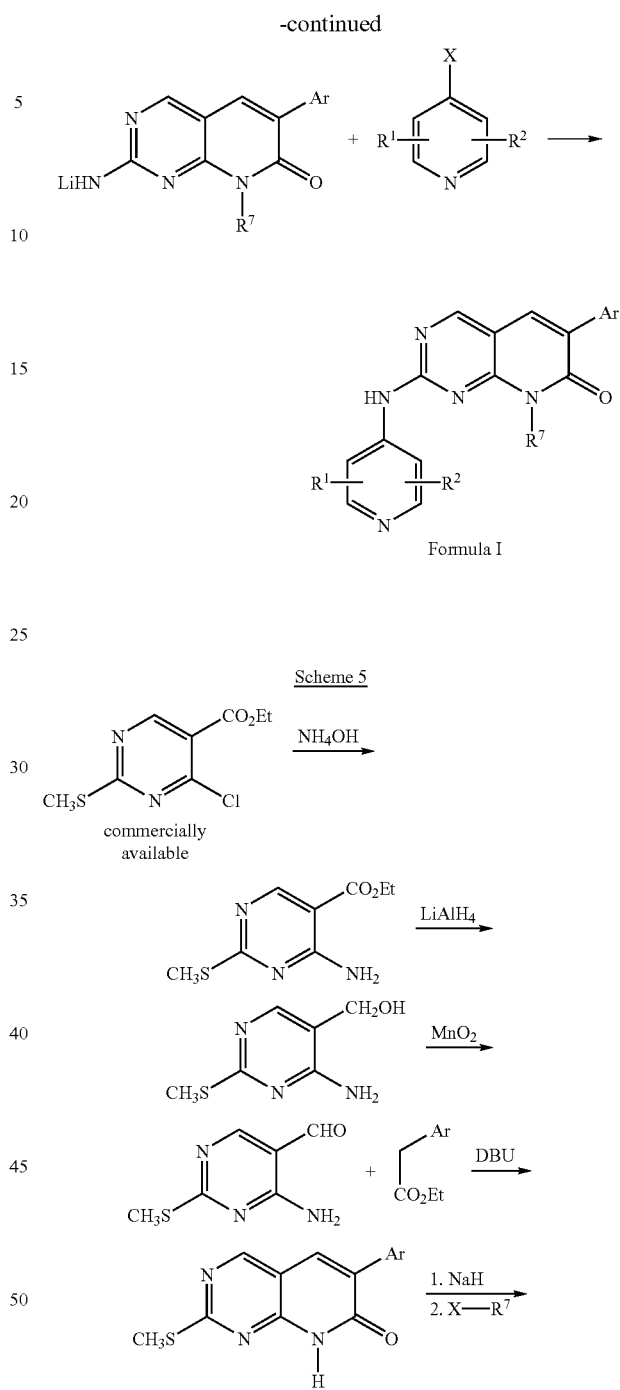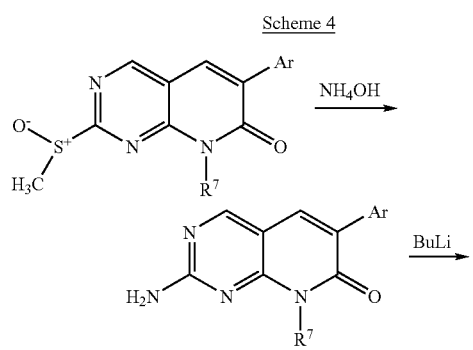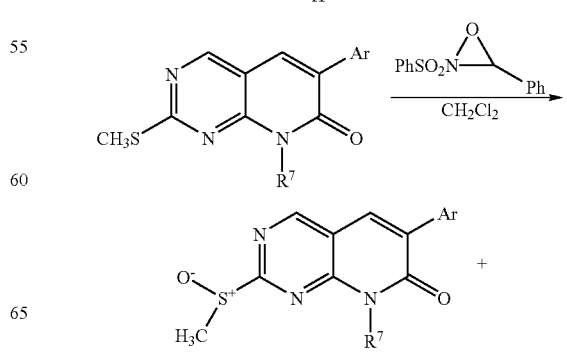

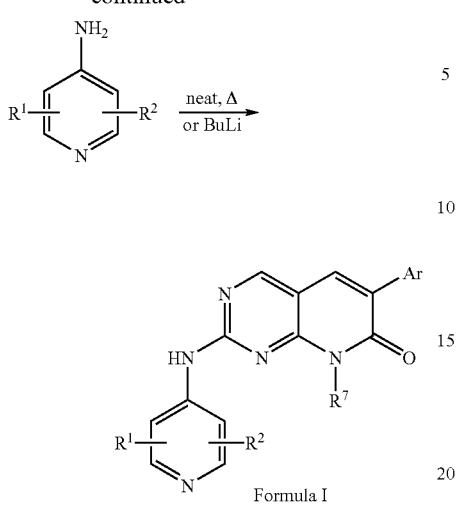

Formula I

Scheme 6

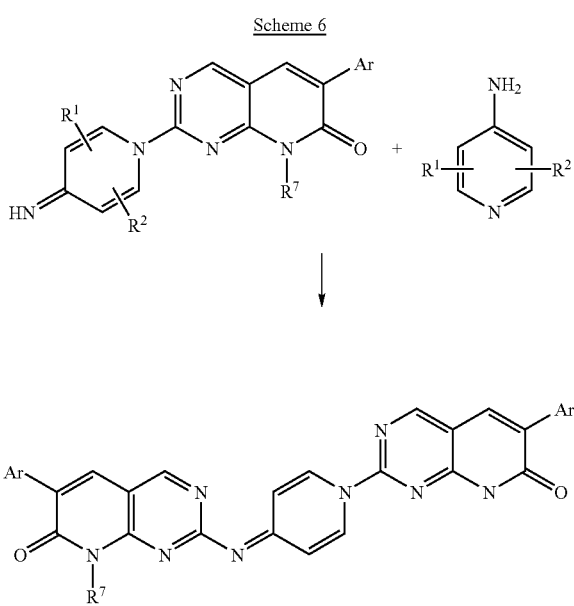

Scheme 7

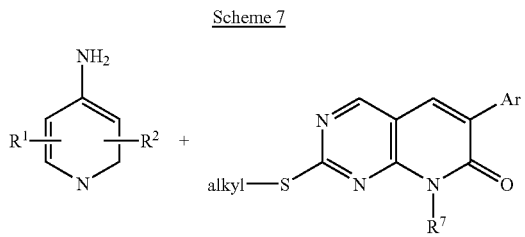

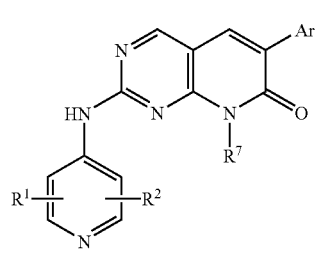

Preferred compounds of Formula I are those wherein $R^1$ and $R^2$ are independently hydrogen, halogen, $C_1$–$C_6$ alkyl, or $C_1$–$C_6$ alkoxy; and more preferably $R^1$ and $R^2$ are independently hydrogen; $R^5$ and $R^6$ are independently hydrogen, halogen, or $C_1$–$C_6$ alkyl; and $R^7$ is $C_1$–$C_6$ alkyl or $C_3$–$C_6$ cycloalkyl. For $R^1$ and $R^2$, it is preferred that halogen is chloro, $C_1$–$C_6$ alkyl is methyl or ethyl and $C_1$–$C_6$ alkoxy is methoxy. For $R^5$ and $R^6$, it is preferred that halogen is chloro, and $C_1$–$C_6$ alkyl is methyl. For $R^7$, it is preferred that $C_1$–$C_6$ alkyl is methyl or ethyl, and more preferably ethyl; and $C_3$–$C_6$ cycloalkyl is cyclopentyl.

The following detailed examples further illustrate synthesis of the compounds of this invention. The examples are illustrative only, and are not to be construed as limiting the invention in any respect.

EXAMPLE 1

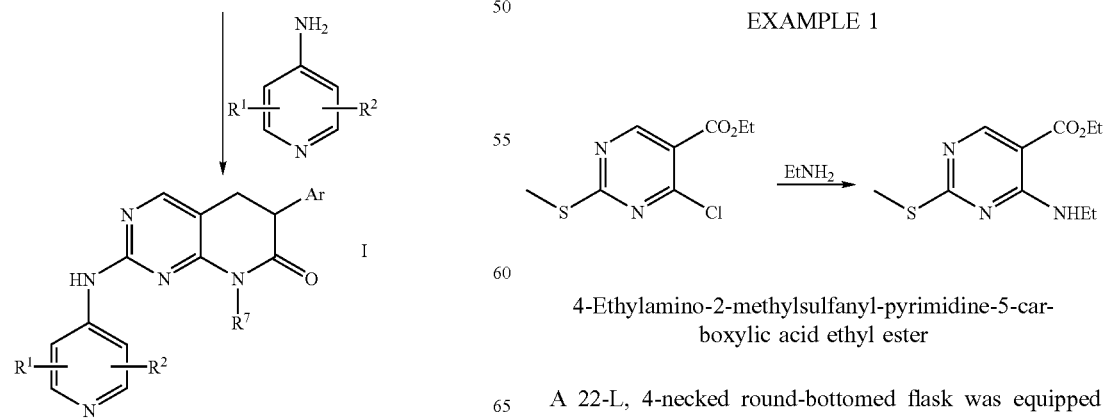

4-Ethylamino-2-methylsulfanyl-pyrimidine-5-carboxylic acid ethyl ester

A 22-L, 4-necked round-bottomed flask was equipped with a mechanical stirrer, a dropping funnel, and a thermometer. The flask was charged with the ethyl 4-chloro-2-

(methylthio)-5-pyrimidinecarboxylate (1.53 kg, 6.56 mol), triethylamine (2.74 L, 19.7 mol, 3 eq), and 7.5 L of tetrahydrofuran to give a solution. The aqueous ethylamine (0.53 L, 6.56 mol, 1 eq) was added via the dropping funnel over 20 minutes. The reaction temperature rose to 35° C. during the addition. The reaction was stirred at ambient temperature for 2 hours. The reaction was checked for completion using TLC (SiO$_2$; 7:3/heptane:ethyl acetate). The precipitate (triethylamine hydrochloride) was filtered off and washed 2 times with tetrahydrofuran, combining the washes with the original filtrate. The tetrahydrofuran was stripped to near dryness on a rotary evaporator. The residue was partitioned between saturated aqueous sodium bicarbonate (500 mL) and ethyl acetate (1 L). Note that there is carbon dioxide gas evolution from the bicarbonate both during the partitioning and the subsequent washes. The layers were separated and the organic layer washed 2 times with saturated aqueous sodium bicarbonate and 1 time with brine. The solution was dried over magnesium sulfate, filtered, and stripped to give the titled compound as an off-white solid. Yield: 95%.

EXAMPLE 2

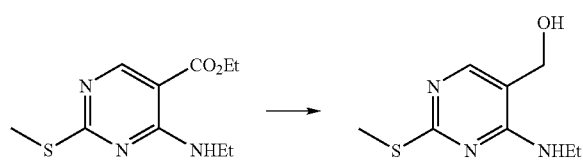

4-Ethylamino-2-methylsulfanyl-pyrimidin-5-yl)-methanol

The 50-L built-in reactor was purged with argon 3 times, and then a positive argon pressure was maintained throughout the process. The reactor was charged with 4 L of tetrahydrofuran, followed by lithium aluminum hydride (1 M in tetrahydrofuran, 6.77 kg, 7.48 L, 7.48 mol, 1.2 eq). The chiller/heater was set to 18° C. and activated. The product of Example 1, 4-ethylamino-2-methylsulfanyl-pyrimidine-5-carboxylic acid ethyl ester (1.5 kg, 6.23 mol, 1 eq), was dissolved in 11 L of tetrahydrofuran (0.58 M) and was added to the reaction vessel using a pump over ~2 hours. TLC (SiO$_2$; 7:3/heptane:ethyl acetate) was used to monitor the reaction for completion. When the reaction was complete, the chiller/heater was set to 10° C. The excess hydride was quenched by adding successively: 1.25 L of water, 1.25 L of 15 wt % sodium hydroxide, and then 4.1 L of water. The first portion of water was added quite slowly and with vigorous stirring to keep down the foaming and to keep the temperature below 30° C. As the quench continues, the addition rate was gradually increased until the final portion of water could be added in a steady stream. The reaction mixture was then stirred for 1 hour before filtering through a 1-inch plug of celite in a 2 L coarse fritted funnel. The salts were washed once with tetrahydrofuran on the funnel. The tetrahydrofuran was stripped, then the residue azeotroped 2 times with 1 L portions of toluene. The resulting solid was washed from the flask using heptane, then dried in a vacuum oven at 40° C. to give the titled compound which is used in the next step without further purification.

EXAMPLE 3

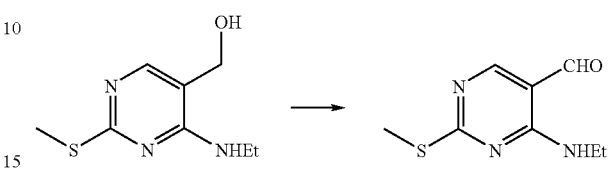

4-Ethylamino-2-methylsulfanyl-pyrimidine-5-carboxaldehyde

A 50-L round-bottomed flask equipped with a mechanical stiffer was charged with 565 g (2.84 mol) of the product of Example 2, 4-ethylamino-2-methylsulfanyl-pyrimidin-5-yl)-methanol, 1.23 kg (14.2 mol, 5 eq) of manganese (IV) oxide, and 19 L of chloroform. The mixture was stirred 24 hours at room temperature, then checked by TLC (SiO$_2$; 7:3/heptane: ethyl acetate) for completion of reaction. The reaction was filtered through a plug of celite and the chloroform stripped to give the titled compound in 90% yield.

EXAMPLE 4

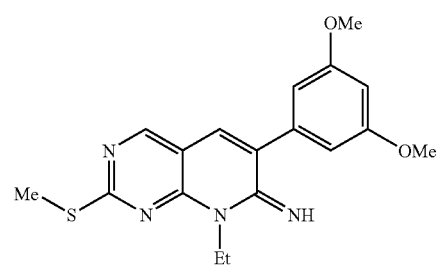

6-(3,5-Dimethoxy-phenyl)-8-ethyl-2-methylsulfanyl-8H-pyrido[2,3-d]pyrimidin-7-ylideneamine To a solution of the product of Example 3, 4-ethylamino-2-methylsulfanyl-pyrimidine-5-carboxaldehyde (37.0 g, 0.19 mol) and 3,5-dimethoxyphenylacetonitrile (37.0 g, 0.21 mol) in DMF (300 mL) was added portionwise anhydrous K$_2$CO$_3$ (130 g) with stirring. The reaction mixture was heated overnight at 105–110° C. and filtered hot. The insoluble salts were washed with DMF (100 mL), and water was added to the warm filtrate until the solution just turned turbid. Crystals developed upon seeding or inducement (scratching with a glass rod). The product was collected by filtration, washed with 100 mL DMF/H$_2$O (25:75), washed with water, and dried in vacuo to afford 50.5 g (76%) of the titled compound. mp 93–95° C.

EXAMPLE 5

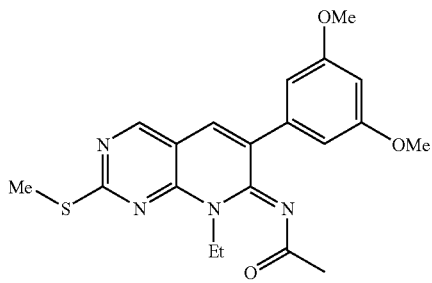

N-[6-(3,5-Dimethoxy-phenyl)-8-ethyl-2-methylsulfanyl-8H-pyrido[2,3-d]pyrimidin-7-ylidene]-acetamide A mixture of the product of Example 4, 6-(3,5-dimethoxy-phenyl)-8-ethyl-2-methylsulfanyl-8H-pyrido[2,3-d]pyrimidin-7-ylideneamine (50.0 g, 0.145 mol), and acetic anhydride (150 mL) were heated with stirring until reflux at which point all the starting material dissolved. The reaction mixture was heated at reflux for 5 minutes, cooled in an ice bath, and t-butyl methyl ether added. The product was collected by filtration, washed with acetic anhydride (50 mL) and ether (100 mL) to afford 43.7 g (78% yield) of the titled compound. mp 145–150° C.

EXAMPLE 6

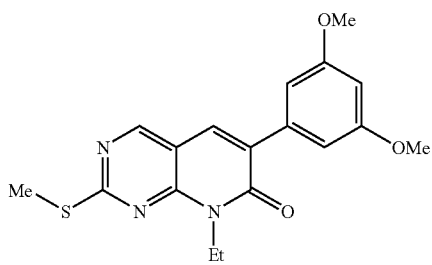

6-(3,5-Dimethoxy-phenyl)-8-ethyl-2-methylsulfanyl-8H-pyrido[2,3-d]pyrimidin-7-one A mixture of the product of Example 5, N-[6-(3,5dimethoxy-phenyl)-8-ethyl-2-methylsulfanyl-8H-pyrido[2,3-d]pyrimidin-7-ylidene]-acetamide, (43.5 g, 0.11 mol) and dioxane (200 mL) was heated with stirring to the boiling point at which point the solid dissolved. At the boiling point was added 100 mL of 15% aq. $H_2SO_4$ and the mixture refluxed for 2 minutes. The reaction mixture cooled in an ice bath and water was added (~200 mL). Crystals formed that were collected by filtration and washed with water. The solid was dissolved in $CH_2Cl_2$ (400 mL), dried over $K_2CO_3$, charcoal added, and the mixture filtered through celite. The filtrate was evaporated under reduced pressure to give 33.0 g of the titled compound. mp 120–122° C.

EXAMPLE 7

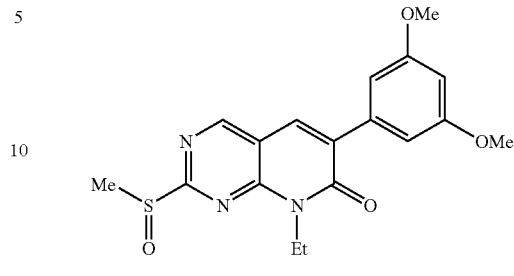

6-(3,5-Dimethoxy-phenyl)-8-ethyl-2-methanesulfinyl-8H-pyrido[2,3-d]pyrimidin-7-one To a solution of the product of Example 6, 6-(3,5-dimethoxy-phenyl)-8-ethyl-2-methylsulfanyl-8H-pyrido[2,3-d]pyrimidin-7-one (17.0 g, 0.048 mol), $CHCl_3$ (150 mL) was added trans-2-phenylsulfonyl-3-phenyloxaziridine (15.2 g, 0.058 mol; *Organic Synthesis* 1987; 66:203–210). The reaction mixture was stirred overnight at room temperature. The product was purified by filtering through a large sintered glass funnel filled with silica gel wetted with $CHCl_3$. The product was eluted off the silica gel with the following order of solvents: $CHCl_3$, EtOAc, $MeOH/CHCl_3$ (1:20), and $MeOH/CHCl_3$ (1:10). The solvent was removed under reduced pressure and the residue taken up in hot EtOAc (40 mL), filtered, and concentrated to 20 mL under reduced pressure. The product separated and was collected by filtration to give 13.77 g of the titled compound, mp 114–116° C.

Alternatively, to a solution of the product of Example 1 or 1A, 2-methylsulfanyl-6-(3,5-dimethoxy-phenyl)-8-ethyl-8H-pyrido[2,3-d]pyrimidin-7-one (536.2 g, 1.50 mol) in $CHCl_3$ (3.4 L), was added trans-2-phenylsulfonyl-3-phenyloxaziridine (431 g, 1.65 mol; *Organic Synthesis*, 1987; 66:203–210). The reaction mixture was stirred overnight at room temperature. Methyl t-Butyl Ether (MTBE) was added to the solution until a precipitate formed (~7 L). The solid was collected by filtration, washed once with MTBE and dried in a vacuum oven at room temperature. Proton NMR (DMSO) is consistent with the structure.

EXAMPLE 8

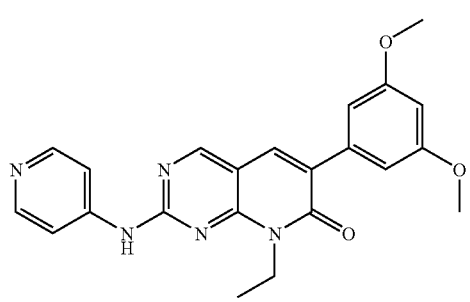

6-(3,5-Dimethoxy-phenyl)-8-ethyl-2-(pyridin-4-ylamino)-8H-pyrido[2,3-d]pyrimidin-7-one A mixture of the product of Example 7, 6-(3,5-dimethoxy-phenyl)-8-ethyl-2-methanesulfinyl-8H-pyrido[2,3-d]pyrimidin-7-one (0.280 g, 10.75 mmol), and 4-aminopyridine (0.5 g, 15.3 mmol) was placed in a small round bottom flask and immersed in an oil bath at 180° C. for 5 minutes with stirring. The reaction mixture was cooled to 20° C. and the mixture triturated with water (10 mL). The insoluble product was filtered and dried in air on the filter. The crude product was purified by column chromatography eluting with a solvent gradient starting with pure chloroform and finishing with methanol/chloroform (1:20). The product was crystallized by suspending it in methanol (10 mL) and adding methylene chloride (30 mL) until a solution resulted. The solution was concentrated on a steam bath to approximately 8 mL in volume. The precipitated product was filtered and washed with methanol (0.5 mL) to afford 112 mg of the titled compound. mp 305–307° C.

Mass Spectrum (APCI) (m+)/z 403.9.

EXAMPLE 9

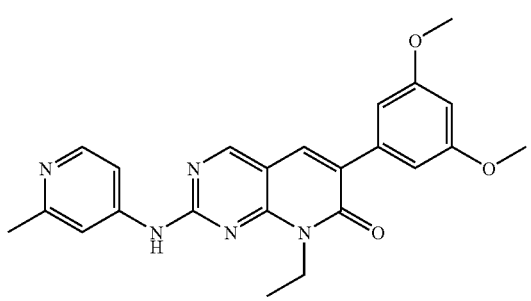

6-(3,5-Dimethoxy-phenyl)-8-ethyl-2-(2-methyl-pyridin-4-ylamino)-8H-pyrido[2,3-d]pyrimidin-7-one To a −78° C. solution of 2.6 g (24.1 mmol) of 4amino-2-methylpyridine in 80 mL of freshly distilled tetrahydrofuran was added 14.0 mL (22.5 mmol) of n-butyllithium over 5 minutes. The reaction mixture was stirred for another 15 minutes, at which time 3.0 g (8.0 mmol) of 6-(3,5-dimethoxy-phenyl)-8-ethyl-2-methylsulfinyl-8H-pyrido[2,3-d]pyrimidin-7-one was added. The mixture was allowed to warm to −10° C. over several hours and stored at −10° C. overnight. An aqueous extraction was performed by pouring the reaction mixture into a separatory funnel containing ethyl acetate, water, and 3.75 mL of 6N HCl. The organic phase was washed twice with water and once with a saturated solution of sodium chloride, dried over magnesium sulfate, filtered, and concentrated. The residue was triturated under 5:50:50 methanol/ethyl acetate/dichloromethane then 1:9 methanol/chloroform and filtered to give 0.79 g (23%) of a pale yellow powder of the titled compound. mp=>300° C.

Mass Spectrum (CI) (m+1)/z 418.

Analysis calculated for: $C_{23}H_{23}N_5O_3 \cdot 0.25\ H_2O$: C, 65.47; H, 5.61; N, 16.60. Found: C, 65.14; H, 5.49; N, 16.28.

EXAMPLE 10

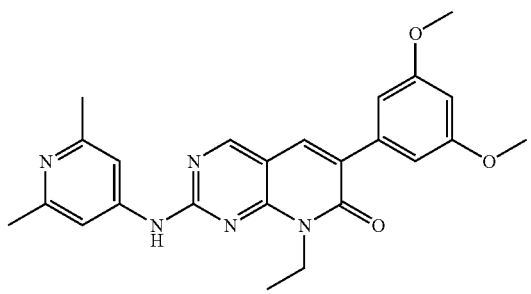

6-(3,5-Dimethoxy-phenyl)-2-(2,6-dimethyl-pyridin-4-ylamino)-8-ethyl-8H-pyrido[2,3-d]pyrimidin-7-one To a −78° C. solution of 3.9 g (32.1 mmol) of 4-amino-2,6-dimethylpyridine in 120 mL of THF was added dropwise 17.5 mL (30.5 mmol) of 1.6 M n-butyllithium in hexanes. The reaction solution was stirred for 15 minutes at which time 3.0 g (8.0 mmol) of the product of Example 7, 6-(3,5-dimethoxy-phenyl)-8-ethyl-2-methanesulfinyl-8H-pyrido[2,3-d]pyrimidin-7-one, was added in small portions as a solid. The reaction mixture was allowed to warm slowly to −10° C. then remain at −10° C. overnight. The reaction mixture was poured into ethyl acetate/water/5 mL 6N HCl. The mixture was shaken and separated. The organic phase was washed with a saturated solution of sodium bicarbonate, twice with water, and brine, then dried over magnesium sulfate, filtered, and concentrated to a solid residue. The residue was triturated under ethyl acetate/dichloromethane. The resulting material was further purified by column chromatography eluting with 5:50:50 methanol/ethyl acetate/dichloromethane to give an orange crystalline material. This material was dissolved in 150 mL of hot 1:9 methanol/chloroform and filtered. The addition of 60 mL of hexane results in the precipitation of 0.99 g (28%) of the title compound as a pale yellow solid.

Analysis calculated for $C_{24}H_{25}N_5O_3 \cdot 0.25\ H_2O$: C, 66.12; H, 5.90; N, 16.06. Found: C, 66.14; H, 5.90; N, 15.92.

EXAMPLE 11

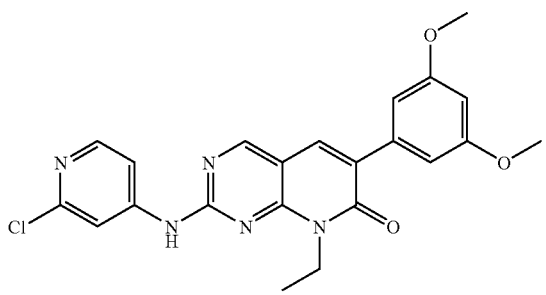

6-(3,5-Dimethoxy-phenyl)-2-(2-chloro-pyridin-4-ylamino)-8-ethyl-8H-pyrido[2,3-d]pyrimidin-7-one

21

To a −78° C. solution of 4.1 g (32.1 mmol) of 4-amino-2-chloropyridine in 120 mL of THF was added dropwise 17.5 mL (30.5 mmol) of 1.6 M n-butyllithium in hexanes. The reaction solution was stirred for 15 minutes at which time 3.0 g (8.0 mmol) of the product of Example 7, 6-(3,5-dimethoxy-phenyl)-8-ethyl-2-methanesulfinyl-8H-pyrido[2,3-d]pyrimidin-7-one, was added in small portions as a solid. The reaction mixture was allowed to warm slowly to −10° C. then remain at −10° C. overnight. The reaction mixture was poured into ethyl acetate/water/5 mL 6N HCl. The mixture was shaken and separated. The organic phase was washed with a saturated solution of sodium bicarbonate, twice with water, and brine, then dried over magnesium sulfate, filtered, and concentrated to a volume of about 200 mL. The suspension was stirred overnight and filtered to give a yellow solid. The solid was triturated under 20 mL of 1:9 methanol/chloroform, filtered, and dried to give 1.89 g (54%) of the titled compound.

Analysis calculated for $C_{22}H_{20}N_5O_3Cl \cdot 0.03\ C_4H_8O_2 \cdot 0.03\ CHCl_3 \cdot 0.03\ CH_3OH$: C, 59.86; H, 4.62; N, 15.74. Found: C, 59.83; H, 4.43; N, 15.69.

EXAMPLE 12

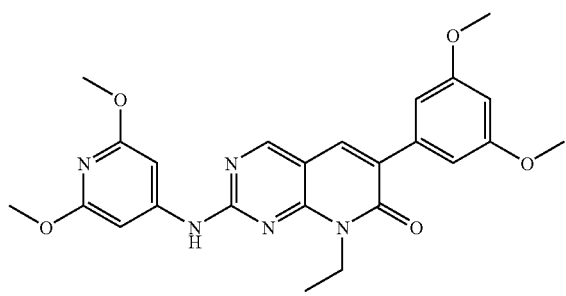

6-(3,5-Dimethoxy-phenyl)-2-(2,6-dimethoxy-pyridin-4-ylamino)-8-ethyl-8H-pyrido[2,3-d]pyrimidin-7-one To a −78° C. solution of 3.0 g (19.5 mmol) of 4-amino-2,6-dimethoxypyridine in 75 mL of THF was added dropwise 10.6 mL (17.0 mmol) of 1.6 M n-butyllithium in hexanes. The reaction solution was stirred for 15 minutes at which time 1.8 g (4.9 mmol) of 6-(3,5-dimethoxy-phenyl)-8-ethyl-2-methylsulfinyl-8H-pyrido[2,3-d]pyrimidin-7-one was added in small portions as a solid. The reaction mixture was allowed to warm slowly to −10° C. then remain at −10° C. overnight. The reaction mixture was poured into ethyl acetate/water/3.5 mL 6N HCl. The mixture is shaken and separated. The organic phase was washed with a saturated solution of sodium bicarbonate, twice with water, and brine, then dried over magnesium sulfate, filtered, and concentrated to a solid yellow residue. The solid was triturated under 25 mL of 1:15:10 methanol/chloroform/ethyl acetate and filtered to give a yellow solid that is crystallized from 300 mL of acetonitrile to give 1.15 g (51%) of the titled compound.

Analysis calculated for $C_{24}H_{25}N_5O_5$: C, 62.19; H, 5.44; N, 15.11. Found: C, 62.10; H, 5.35; N, 15.10.

22

EXAMPLE 13

2-(Pyridin-4-ylamino)-6-(3,5-dimethoxyphenyl)-8-ethyl-8H-pyrido[2,3-d]-pyrimidin-7-one hydrochloride (by Scheme 7)

To a solution of 88 g (0.93 mol) of 4-aminopyridine in 1 L of tetrahydrofuran was added 21.2 g (2.67 mol) of lithium hydride. The reaction mixture was heated to 50° C. for 1 hour. To the stirred reaction mixture was added a solution of 318 g (0.89 mol) of 2-(methylsulfanyl)-6-(3,5-dimethoxyphenyl)-8-ethyl-8H-pyrido[2,3-d]pyrimidin-7-one in 1.8 L of tetrahydrofuran. The reaction solution was heated at reflux for 24 hours, and then cooled to 50° C. The reaction mixture was diluted by the slow addition of a mixture of 500 mL of water and 1 L of 6N hydrochloric acid. The reaction mixture was cooled to 24° C. and stirred for 16 hours. The reaction mixture was further diluted by addition of 250 mL of acetonitrile and 200 mL of water, and stirring was continued for an additional 2 hours. The mixture was then filtered, and the filter cake was dried at 45° C. in vacuo for 12 hours to provide 360 g (92%) of 2-(pyridin-4-ylamino)-6-(3,5-dimethoxyphenyl)-8-ethyl-8H-pyrido[2,3-d]pyrimidin-7-one hydrochloride, mp 295–300° C. (dec). HPLC established the purity at 98%. Mass Spec (APCI) 439.89 m/z.

By following the general procedures described above, the following additional invention compounds were prepared:

EXAMPLE 14

6-(2-Chloro-3,5-dimethoxy-phenyl)-2-(pyridin-4-ylamino)-8-ethyl-8H-pyrido[2,3-d]pyrimidin-7-one; mp 264≧272° C.

EXAMPLE 15

6-(2,6-Dichloro-3,5-dimethoxy-phenyl)-2-(pyridin-4-ylamino)-8-ethyl-8H-pyrido[2,3-d]pyrimidin-7-one; mp 295.5–297.0° C.

EXAMPLE 16

6-(3,5-Dimethoxy-phenyl)-2-(pyridin-4-ylamino)-8-cyclopentyl-8H-pyrido[2,3-d]pyrimidin-7-one; mp 283–285° C.

EXAMPLE 17

6-(3,5-Dimethoxy-phenyl)-2-(pyridin-4-ylamino)-8-methyl-8H-pyrido[2,3-d]pyrimidin-7-one; mp 245–247° C.

EXAMPLE 18

6-(3,5-Dimethoxy-phenyl)-2-[2-(4-methylpiperizinyl)pyridin-4-ylamino]-8-ethyl-8H-pyrido[2,3-d]pyrimidin-7-one

EXAMPLE 19

6-(3,5-Dimethoxy-phenyl)2-[2-(2-dimethylaminoethoxy)-pyridin-4-ylamino-]-8-ethyl-8H-pyrido[2,3-d]pyrimidin-7-one

EXAMPLE 20

6-(3,5-Dimethoxy-phenyl)-2-[2-(2-diethylaminoethylamino)-pyridin4-ylamino]-8-ethyl-8H-pyrido[2,3-d]pyrimidin-7-one As noted above, the compounds of Formula I are useful for treating diseases or disease states such as cancer and other proliferative diseases which include, but are not limited to, psoriasis, restenosis, and atherosclerosis. The invention compounds are especially useful for treating restenosis following balloon angioplasty of occluded arteries. Restenosis occurs in about 40% of individuals undergoing angioplasty of calcified arteries and is a major problem associated with this form of treatment of patients suffering from such cardiac condition.

The term "treating" for purposes of the present invention refers to prophylaxis or prevention, amelioration or elimination of a named condition once the condition has been established.

The term "mammal" for purposes of the present invention includes humans, cows, dogs, cats, goats, sheep, and pigs. Preferably, the mammal is human.

The compounds of the present invention can be formulated and administered in a wide variety of oral and parenteral dosage forms, including transdermal and rectal administration. It will be recognized to those skilled in the art that the following dosage forms may comprise as the active component, either a compound of Formula I or a corresponding pharmaceutically acceptable salt or solvate of a compound of Formula I.

A further embodiment of this invention is a pharmaceutical formulation or composition comprising a compound of Formula I together with a carrier, diluent, or excipient thereof, such as a pharmaceutically acceptable carrier, diluent, or excipient. For preparing pharmaceutical compositions with the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid such as talc or starch, which is in a mixture with the finely divided active component.

In tablets, the active component is mixed with the carrier having the necessary binding properties in suitable proportions and compacted in the shape and size desired.

The formulations or compositions of this invention preferably contain from about 5% to about 70% or more of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. A preferred form for oral use are capsules, which include formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water-propylene glycol solutions. For parenteral injection, liquid preparations can be formulated in solution in aqueous polyethylene glycol solution, isotonic saline, 5% aqueous glucose, and the like.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with a viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Waxes, polymers, microparticles, and the like can be utilized to prepare sustained-release dosage forms. Also, osmotic pumps can be employed to deliver the active compound uniformly over a prolonged period.

The pharmaceutical preparations of the invention are preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

An "effective amount" is an amount of a compound of the present invention that when administered to a patient treats a disease state, such as restenosis, cancer, atherosclerosis, or angiogenesis. An "antiangiogenic effective amount" is an amount of a compound of the present invention that when administered to a patient treats angiogenesis.

The therapeutically effective dose or effective amount of a compound of Formula I will generally be from about 1 mg to about 100 mg/kg of body weight per day. Typical adult doses will be about 50 to about 800 mg per day. The quantity of active component in a unit dose preparation may be varied or adjusted from about 0.1 mg to about 500 mg, preferably about 0.5 mg to 100 mg according to the particular application and the potency of the active component. The composition can, if desired, also contain other compatible therapeutic agents. A subject in need of treatment with a compound of Formula I will be administered a dosage of about 1 to about 500 mg per day, either singly or in multiple doses over a 24-hour period.

EXAMPLE 21

A pharmaceutical formulation in the form of hard gelatin capsules for oral administration are prepared using the following ingredients:

| | Quantity (mg/capsule) |
|---|---|
| Active compound | 250 |
| Starch powder | 200 |
| Magnesium stearate | 10 |
| Total | 460 mg |

The above ingredients are mixed and filled into hard gelatin capsules in 460 mg quantities. A typical active ingredient is 6-(3,5-dimethoxyphenyl)-2-(2,6-dimethylpyridin-4-ylamino)-8-cyclopropyl-8H-pyrido[2,3-d]pyrimidin-7-one. The composition is administered from 2 to 4 times a day for treatment of postsurgical restenosis.

EXAMPLE 22

| Formulation for Oral Suspension | |
|---|---|
| Ingredient | Amount |
| 6-(3,5-Dimethoxy-phenyl)-2-(2,6-dimethyl-pyridin-4-ylamino)-8-ethyl-8H-pyridol[2,3-d]pyrimidin-7-one. | 500 mg |
| Sorbitol solution (70% N.F.) | 40 mL |
| Sodium benzoate | 150 mg |
| Saccharin | 10 mg |
| Cherry flavor | 50 mg |
| Distilled water q.s. ad | 100 mL |

The sorbitol solution is added to 40 mL of distilled water, and the pyridopyrimidine is suspended therein. The saccharin, sodium benzoate, and flavoring are added and dissolved. The volume is adjusted to 100 mL with distilled water. Each milliliter of syrup contains 5 mg of active ingredient.

EXAMPLE 23

| Tablets each containing 60 mg of active ingredient | |
|---|---|
| Active ingredient | 60 mg |
| Starch | 45 mg |
| Microcrystalline cellulose | 35 mg |
| Polyvinylpyrolidone (as 10% solution in water) | 4 mg |
| Sodium carboxymethyl starch | 4.5 mg |
| Magnesium stearate | 0.5 mg |
| Talc | 1.0 mg |
| Total | 150 mg |

The active ingredients, starch and cellulose, are passed through a No. 45 mesh U.S. sieve and mixed thoroughly. The solution of polyvinylpyrolidone is mixed with the resultant powders and then passed through a No. 14 mesh U.S. sieve. The granules are dried at 50° C. to 60° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

A typical active ingredient utilized in the above preparation is the compound of Example 12.

EXAMPLE 24

A parenteral composition suitable for administration by injection is prepared by dissolving 100 mg of 2-(pyridin-4-ylamino)-6-(3,5-diisopropoxyphenyl)-8-isobutyl-8H-pyrido[2,3-d]pyrimidin-7-one in 250 mL of 0.9% aqueous sodium chloride solution and adjusting the pH of the solution to about 7.0. This formulation is well suited for the treatment of breast cancer.

EXAMPLE 25

Preparation for Suppositories

A mixture of 500 mg of 2-(pyridin4ylamino)-6-(3,5-dimethoxyphenyl)-pyrido[2,3-d]pyrimidin-7(8H)-one and 1500 mg of theobroma oil are blended to uniformity at 60° C. The mixture is cooled to 24° C. in tapered molds. Each suppository will weigh about 2 g and can be administered from 1 to 2 times each day for treatment of bacterial infections.

EXAMPLE 26

Slow Release Preparation

Five hundred milligrams of 6-(3,5-diethoxyphenyl)-2-(2,6-diethylpyridin-4-ylamino)-8-ethyl-8H-pyrido[2,3-d]pyrimidin-7-one hydrochloride was placed in an osmotic pump tablet and administered orally for treatment and prevention of restenosis.

The invention compounds have been evaluated in the in vitro biological assays described in U.S. Pat. No. 5,733,914. They have been compared with representative compounds from the U.S. Pat. No. 5,733,914 patent and have exhibited greater selectivity for inhibiting VEGF and FGF, without inhibiting the Src family kinases c-Src and Lck. For example, the data in Table 1 below shows a comparison of Example 8 of the present invention with two compounds embraced by U.S. Pat. No. 5,733,914. Reference Compound A has a 2,6-dichloro phenyl group at the 6-position. Reference Compound B has a 3,5-dimethoxyphenyl group at the 6-position and a substituted phenylamino at the 2-position. The invention compound of Example 8 has the required 3,5-dimethoxyphenyl at the 6-position and the required (4-pyridyl)amino at the 2-position. The structures are shown in Table 1, along with their respective inhibitory activities against various tyrosine kinases, when evaluated in the models described in U.S. Pat. No. 5,733,914.

Kinase Inhibition Assays

TABLE 1

Structures of Reference Compounds A and B, and of Invention Compound of Example 8, and Comparative Kinase Inhibition Activities

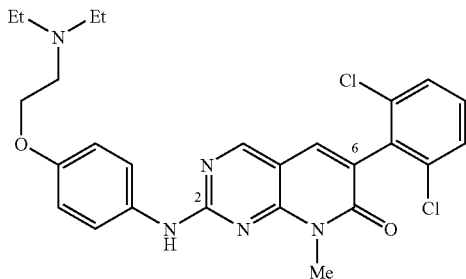

Reference Compound A

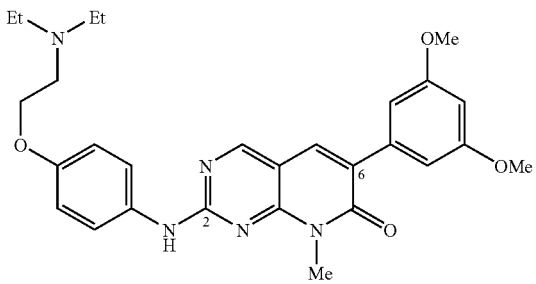

Reference Compound B

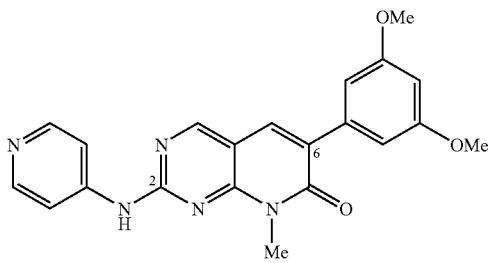

Example 8

| | Kinase Inhibition Data | | | | |
|---|---|---|---|---|---|
| Compound | FGFr ($IC_{50} = \mu M$) | (VEGF-2) ($IC_{50} = \mu M$) | PDGF ($IC_{50} = \mu M$) | Lck ($K_i = \mu M$) | c-Src ($IC_{50} = \mu M$) |
| Reference A | 0.004 | 0.009 | 0.085 | 0.013 | 0.003 |
| Reference B | 0.002 | 0.004 | 0.46 | 0.06 | 1.34 |
| Example 8 | 0.009 | 0.020 | 2.54 | 1.79 | 36.5 |

The kinase inhibition data in Table 1 establish that the compound of Example 8 is more selective in its activity for VEGFR-2 and FGFR-1 (nM $IC_{50}$ values) compared to PDGFR, Lck, and c-Src ($\mu M$ $IC_{50}$ values) than the reference Compounds A and B. The reference compounds potently inhibit all five tyrosine kinases to a similar degree, which could result in an increased incidence of undesired side effects from therapy of the more selective compound. The preferred kinase selectivity profile of the compound in Example 8 is shared by the other representative compounds of the invention shown in Table 2. The inhibition activity of the compounds in Examples 8, 9, 10, 11, and 12 and Reference Compounds A and B were evaluated using the Dissociated Enhanced Lanthanide Fluoroimmuno Assay (DELFIA) (Frank Loganzo and Carolyn Hardy. A sensitive, time-resolved fluorometric assay for the detection of inhibitors of phosphotyrosine kinases. *American Biotechnology Laboratory*, December 1998). DELFIA plates (EG&G Wallac, Gaithersburg, Md.) were coated overnight with Poly Glu Tyr (4:1) (Sigma, St. Louis, Mo.) at room temperature, washed (DELFIA wash reagent, EG&G Wallac), and spotted with 1 μL inhibitor dilution or DMSO carrier control per well. In some cases, kinase was autophosphorylated prior to analysis by incubating 45 minutes at 4° C. in the presence of 4 mM ATP and 25 mM $MgCl_2$. A typical 100 μL kinase assay reaction contained 20 mM Tris (pH 7.5), 20 mM $MgCl_2$, 50 mM NaCl, 5 mM DTT, and protease inhibitors (Mini EDTA-free protease inhibitor cocktail tablets, Boehringer Mannheim, Indianapolis, Ind.), 40 µM ATP, and an appropriate concentration of inhibitor. The reaction was allowed to continue for 30 minutes at room temperature. Plates were washed, blocked 30 minutes at room temperature (0.5% bovine serum albumin in DELFIA Assay Buffer, EG&G Wallac), and washed. One hundred microliter europium-conjugated antiphosphotyrosine antibody in DELFIA assay buffer was added to each well. Plates were incubated for 1 hour and decanted. One hundred microliter DELFIA enhancement solution (EG&G Wallac) was added and time-resolved fluorescence of the reactions determined using a VICTOR2 1420 multilable counter (EG&G Wallac). Compounds were tested from 10 through 0.0001 µM. c-Src was (Upstate Biotechnology, Lake Placid, N.Y.) was used at 3 units per reaction. The kinase domains from FGFR-1, VEGFR-2, Lck, and PDGF were purified from baculoviral vectors expression systems and were used in the assays at 20 nM.

TABLE 2

Kinase Inhibition Data

| Example No. | FGFr ($IC_{50}$ = µM) | (VEGF-2) $IC_{50}$ = µM | PDGF ($IC_{50}$ = µM) | Lck (Ki = µM) | c-Src ($IC_{50}$ = µM) |
|---|---|---|---|---|---|
| 8 | 0.009 | 0.020 | 2.54 | 1.79 | 36.5 |
| 9 | | | | | |
| 10 | 0.0008 | 0.001 | | 0.74 | >4 |
| 11 | 0.0002 | 0.003 | 5 | 2.77 | >4 |
| 12 | | | | | |

Cellular Proliferation Assays

Human umbilical vein endothelial cells (HUVECs) (Clonetics, Palo Alto, Calif.) were seeded at 2000 cells per well in growth medium containing 2% serum (EGM, Clonetics) and allowed to attach overnight (37° C., 5% $CO_2$, 100% humidity). C6 rat glioma cells (ATCC) were seeded at 600 cells per well and incubated in F10 medium (GIBCO, Gaithersburg, Md.) supplemented with 15% horse serum, 2.5% fetal bovine serum, and 1 mM glutamine. A90 human ovarian cells (Dr. Kent Crickard, SUNY/AB Medical School) were seeded at 600 cells per well in RPMI1640 (GIBCO) plus 10% fetal bovine serum. Plates were incubated overnight (37° C., 5% $CO_2$, 100% humidity) to allow the cells to attach. Test compound dilutions were added to the appropriate wells, and the incubation was continued for 4 additional days. Monolayers were fixed in 10% trichloroacetic acid (30 minutes at 4° C.), washed with distilled water, and stained with Sulphorhodamine B (0.075% in 1% acetic acid) (Sigma). Plates were washed in 1% acetic acid, and the bound dye was solubilized in 100 µL unbuffered Tris base. Absorbance was measured at 540 nm using a reference filter wavelength of 630 nm. Inhibitor potency ($IC_{50}$) versus cellular proliferation was determined, and endothelial cell selectivity was assessed by comparing the inhibition of HUVEC proliferation to A90 and C6 tumor cell proliferation (Table 3). The compounds in Examples 8, 9, 10, 11, and 12 are selective inhibitors of serum-stimulated endothelial cell proliferation in cell culture.

TABLE 3

Inhibition of Serum Stimulated HUVEC Cell Proliferation

| Example | HUVEC (Serum) ($IC_{50}$ = µM) | A90 ($IC_{50}$ = µM) | C6 ($IC_{50}$ = µM) |
|---|---|---|---|
| 8 | 0.009 | 2.92 | >25 |
| 9 | | | |
| 10 | | | |
| 11 | 0.013 | 25.00 | 9.68 |
| 12 | | | |

Permeability Studies

Cell transport studies were conducted with Caco-2 cells grown on Snapwells™ between 22 and 28 days postseeding. Typically, 10 mM MES buffer (pH 6.5) with 5 mM KCl, 135 mM NaCl, and 1.8 mM $CaCl_2$ was used for the apical side and 10 mM MOPS (pH 7.4) with 5 M KCl, 132 mM NaCl, and 1.8 mM $CaCl_2$ with 5 mM D-glucose was used for the basolateral side. On the day of the experiment, the growth media was aspirated, and the cell monolayers were pre-equilibrated with appropriate buffers at 37° C., and TEER measurements were performed to confirm the integrity of the monolayers. Transepithelial flux measurements were made by mounting the cell monolayers in a side-by-side diffusion chamber system (Precision Instrument Design, Tahoe City, Calif.). Temperature was maintained at 37° C. with a circulating water jacket. The solutions were mixed with gas-lift circulation with 95% oxygen/5% carbon dioxide. Donor solutions were mixed with test compounds, $^{14}C$ mannitol (leakage marker) and $^3H$ metoprolol (reference compound), and added to the apical chamber. Donor and receiver samples were collected at selected time intervals for up to 3 hours. Radiolabeled mannitol and metoprolol were analyzed using scintillation counting (Top Count, Packard Instruments, Downers Grove, Ill.). Test compounds were analyzed using LC-MS/MS methods. Apparent permeability coefficients were calculated using the following equation:

$$Papp = (V \cdot dC/dt)/(A \cdot C_0)$$

where V=volume of the receiver solution in mL; A=surface area of the monolayer in $cm^2$; $C_0$=initial donor concentration in mM; and dC/dt=change of the drug concentration in the receiver chamber over time.

Compounds with permeabilities similar or greater than metoprolol (~30·10−6 cm/sec; absorption 90%) are assumed to have the potential for essentially complete absorption.

Metabolic Stability Studies

Compounds were individually incubated (5 µM in DMSO) with human and mice liver S9 fractions in 50 mM $KHPO_4$ buffer at 37° C. in the presence of 1.0 mM NADPH and additional cofactors. At 0, 10, 20, and 40 minutes, 100 µL aliquots were removed and added to 300 µL of acetonitrile. Standard curves were prepared in a similar manner with each compound. Samples were analyzed for parent concentration by LC-MS/MS. The in vitro metabolic half-life was determined from the concentration-time plots using WinNonlin. These in vitro data represent the rate of oxidative, hydrolytic, and conjugative metabolism. Compounds demonstrating half-lives above 50 minutes are considered to have the potential for being metabolically stable in vivo.

The results of the foregoing permeability and metabolic studies for Reference Compounds A and B, and for the invention compound of Example 8, are presented below in Table 4.

TABLE 4

In Vitro Metabolic Stability and Transport

| Parke-Davis No. | MS9 min | HS9 min | A to B $10^{-6}$ cm/s |
|---|---|---|---|
| Reference A | 14 | 46 | 37.2 |
| Reference B | 10 | 22 | 20.1 |
| Example 8 | >200 | >200 | 398 |

Antitumor Activity In Vivo

The anticancer efficacy of the compound of Example 8 was evaluated using a murine mammary adenosarcoma tumor model, M16/C. This highly vascularized tumor is very aggressive with a doubling time of 1.5 days. Tumor fragments were implanted by trocar fragment in the right axilla of C3H mice on Day 0. The efficacy of treatment was assessed both in an advanced stage model (test compound treatment for nine consecutive days after tumors had reached 100 mg). The compound in Example 8 was dosed once a day over the treatment period by oral gavage in 0.05 M sodium lactate buffer, pH 4. Animals were allowed to continue off therapy until the tumors reached the evaluable size (750 mg). Animal weights were determined throughout the study to provide an estimate of test compound toxicity. A mean weight loss >10% (3–4 g) for any treatment group is an indication of host toxicity. Anticancer activity was evaluated using two methods. The first is %T/C where T=median mass of treated tumors 3 days after the end of therapy, and C=median mass of the control group at that same time point. The highest degree of antitumor activity using this assessment occurs when T=0, and %T/C=0%. A value less than 40% describes meaningful anticancer activity. The second method uses tumor growth delay (T–C), where T=the days for the median treated tumor to reach an evaluable size (750 mg), and C=days for control tumors to reach that same size. As shown in Table 5, the compound of Example 8 was well-tolerated and demonstrated meaningful anticancer activity at all four doses tested (%T/C). Tumor growth delay (T–C) was greater than the duration of therapy for the 40 and 20 mg/kg dose levels, and treatment at those doses yielded complete regressions (regression of tumors below the level of palpation) in this model.

TABLE 5

In Vivo Effectiveness of Example 8 Against Mammary Adenocarcinoma M16/C

| Compound | Dose (mg/kg) | Treatment Schedule | Body Weight Change (g)[a] | T/C (%)[b] | T-C (Days)[c] | CRs[d] | NSD[e] |
|---|---|---|---|---|---|---|---|
| Example 8 | 40 | D7-15[f] | −1.5 | 0 | 12.4 | 6/6 | 0/6 |
| | 20 | | −0.02 | 0 | 10.7 | 4/6 | 0/6 |
| | 10 | | −0.5 | 15 | 7.9 | | 0/6 |
| | 5 | | + | 39 | 4.3 | 0/6 | |

Median/mean time for control tumors to reach 750 mg: 10.6/10.7 days.
[a]Maximum treatment-induced weight loss. A "+" indicates a net weight gain.
[b]Median treated tumor mass/median control tumor mass × 100%
[c]The difference, in days, for the median treated and control tumors to reach 750 mg, respectively
[d]Complete regression, regression of an established tumor to a nonpalpable size
[e]NSD, nonspecific deaths/total in treatment group
[f]Tumor mass at first Rx: 100 mg

What is claimed is:

1. A compound of Formula I

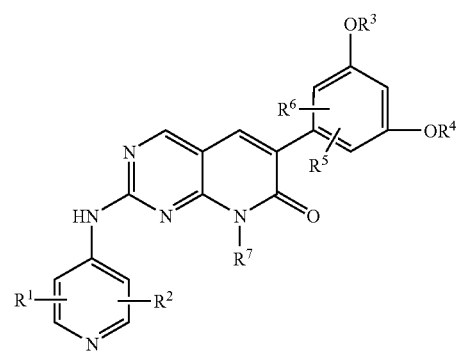

wherein:
 $R^1$, $R^2$, $R^5$, and $R^6$ independently are hydrogen, halogen, $C_1$–$C_6$ alkyl, $C_1$–$C_6$ alkoxy, hydroxy, $C_1$–$C_6$ alkanoyl, —CN, —NO$_2$, $C_1$–$C_6$ alkanoyloxy, COOR$^8$, —CF$_3$, NR$^8$R$^9$, or (X)$_m$-(CH$_2$)$_n$—NR$^8$R$^9$, where $R^8$ and $R^9$ independently are hydrogen, $C_1$–$C_6$ alkyl, $C_1$–$C_6$ alkanoyl, or $R^8$ and $R^9$ taken together with the nitrogen to which they are attached can complete a ring having 3 to 7 carbon atoms and optionally containing 1, 2, or 3 ring heteroatoms selected from the group consisting of nitrogen, substituted nitrogen, oxygen, and sulfur;
 X is NH or O;
 m is 0 or 1;
 n is 0 to 6; provided m and n are not both 0;
 $R^3$ and $R^4$ independently are $C_1$–$C_6$ alkyl or halo substituted $C_1$–$C_6$ alkyl;
 $R^7$ is hydrogen, $C_1$–$C_6$ alkyl, $C_2$–$C_6$ alkenyl, $C_2$–$C_6$ alkynyl, or $C_3$–$C_6$ cycloalkyl.

2. A compound of claim 1 wherein $R^1$ and $R^2$ are independently hydrogen, halogen, $C_1$–$C_6$ alkyl, or $C_1$–$C_6$ alkoxy.

3. A compound of claim 2 wherein the halogen is chloro.

4. A compound of claim 2 wherein the $C_1$–$C_6$ alkyl is methyl or ethyl.

5. A compound of claim 2 wherein the $C_1$–$C_6$ alkoxy is methoxy.

6. A compound of claim 1 wherein $R^1$ and $R^2$ are hydrogen.

7. A compound of claim 1 wherein wherein $R^5$ and $R^6$ are independently hydrogen, halogen, or $C_1$–$C_6$ alkyl.

8. A compound of claim 7 wherein the halogen is chloro.

9. A compound of claim 7 wherein the $C_1$–$C_6$ alkyl is methyl.

10. A compound of claim 1 wherein $R^7$ is $C_1$–$C_6$ alkyl or $C_3$–$C_6$ cycloalkyl.

11. A compound of claim 10 wherein the $C_1$–$C_6$ alkyl is ethyl.

12. A compound of claim 10 wherein the $C_3$–$C_6$ cycloalkyl is cyclopentyl.

13. A compound of claim 1 wherein $R^1$, $R^2$, $R^5$, and $R^6$ all are hydrogen.

14. A compound of claim 1 wherein $R^3$ and $R^4$ both are methyl.

15. A compound of claim 1 wherein $R^7$ is $C_1$–$C_6$ alkyl.

16. The compound 6-(3,5-dimethyoxy-phenyl)-8-ethyl-2-(pyridine-4-ylamino)-8H-pyrido[2,3-d]pyrimidine-7-one.

17. The compound which is:

6-(3,5-Dimethoxy-phenyl)-2-(2-methyl-pyridin-4-ylamino)-8-ethyl-8H-pyrido[2,3-d]pyrimidin-7-one;

6-(3,5-Dimethoxy-phenyl)-2-(2,6-dimethyl-pyridin-4-ylamino)-8-ethyl-8H-pyrido[2,3-d]pyrimidin-7-one;

6-(3,5-Dimethoxy-phenyl)-2-(2-chloro-pyridin-4-ylamino)-8-ethyl-8H-pyrido[2,3-d]pyrimidin-7-one;

6-(3,5-Dimethoxy-phenyl)-2-(2,6-dimethoxy-pyridin-4-ylamino)-8-ethyl-8H-pyrido[2,3-d]pyrimidin-7-one;

6-(3,5-Dimethoxy-phenyl)-2-(pyridin-4-ylamino)-8-methyl-8H-pyrido[2,3-d]pyrimidin-7-one;

6-(2-Chloro-3,5-dimethoxy-phenyl)-2-(pyridin-4-ylamino)-8-ethyl-8H-pyrido[2,3-d]pyrimidin-7-one;

6-(2,6-Dichloro-3,5-dimethoxy-phenyl)-2-(pyridin-4-ylamino)-8-ethyl-8H-pyrido[2,3-d]pyrimidin-7-one;

6-(3,5-Dimethoxy-phenyl)-2-(pyridin-4-ylamino)-8—cyclopentyl-8H-pyrido[2,3-d]pyrimidin-7-one;

6-(3,5-Dimethoxy-phenyl)-2-[2-(4-methylpiperizinyl)pyridin-4-ylamino]-8-ethyl-8H-pyrido[2,3-d]pyrimidin-7-one;

6-(3,5-Dimethoxy-phenyl)-2-[2-(2-dimethylaminoethoxy)-pyridin-4-ylamino]-8-ethyl-8H-pyrido[2,3-d]pyrimidin-7-one; and 6-(3,5-Dimethoxy-phenyl)-2-[2-(2-diethylaminoethylamino)-pyridin-4-ylamino]-8-ethyl-8H-pyrido[2,3-d]pyrimidin-7-one.

18. A pharmaceutical composition comprising a compound of claim 1 together with an excipient, carrier or diluent thereof.

19. A pharmaceutical composition comprising 6-(3,5-dimethoxy-phenyl)-8-ethyl-2-(pyridine-4-ylamino)-8H-pyrido[2,3-d]pyrimidine-7-one together with an excipient, carrier, or diluent thereof.

20. A method of treating uncontrolled angiogenesis in a mammal comprising administering to the mammal in need of treatment an antioangiogenic effective amount of a compound of claim 1.

* * * * *